(12) United States Patent
Yosten (10) Patent No.: US 9,146,240 B2
(45) Date of Patent: Sep. 29, 2015

(54) SYSTEMS AND METHODS FOR DETERMINING A C-PEPTIDE RECEPTOR, C-PEPTIDE RECEPTOR, AND METHODS OF USING SAME

(71) Applicant: Saint Louis University, St. Louis, MO (US)

(72) Inventor: Gina L. C. Yosten, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 14/017,482

(22) Filed: Sep. 4, 2013

(65) Prior Publication Data

US 2014/0072977 A1    Mar. 13, 2014

Related U.S. Application Data

(60) Provisional application No. 61/696,646, filed on Sep. 4, 2012.

(51) Int. Cl.
*G01N 33/566* (2006.01)
*G01N 33/68* (2006.01)

(52) U.S. Cl.
CPC .............. *G01N 33/68* (2013.01); *G01N 33/566* (2013.01); *G01N 2333/726* (2013.01)

(58) Field of Classification Search
CPC   G01N 33/566;  G01N 33/68;  G01N 2333/726
See application file for complete search history.

(56) References Cited

U.S. PATENT DOCUMENTS 7,341,840 B2 *    3/2008   Serhan et al. .................. 435/7.2

OTHER PUBLICATIONS

Yosten et al., Evidence for an interaction of neuronostatin with the orphan G protein-coupled receptor, GPR107, Nov. 1, 2012, Am J Physiol Regul Integr Comp Physiol 303: R941-R949.*
Frei et al., Direct identification of ligand-receptor interactions on living cells and tissues, Oct. 2012, Nature Biotechnology 30(10):997-1003.*
Yosten, Gina L.C., et al., "Evidence for an interaction between proinsulin C-peptide and GPR146," Society for Endocrinology, http://joe.endocrinology-journals.org, Jun. 11, 2013, pp. B1-B8, Bioscientifica, Ltd., Great Britain.

* cited by examiner

*Primary Examiner* — John Ulm
(74) *Attorney, Agent, or Firm* — Lewis Rice LLC (57) ABSTRACT

Systems and methods for the determination of a peptide receptor. Specifically to determine a receptor for any peptide provided that the receptor is a G protein coupled receptor (GPCR).

4 Claims, 8 Drawing Sheets

| Receptor | NCBI ACC | Mix# | KATOIII Cells (Individually) | HEK293 Cells (Individually) | TF-1 Cells (Individually) |
|---|---|---|---|---|---|
| CD97 | NM_078481 | 1 | + | M+ | + |
| CMKLR1 | NM_004072 | 10 | + | + | + |
| FY (DARC) | NM_002036 | 10 | + | + | + |
| GPR107 | NM_001136557.1 | 11 | + | + | + |
| GPR125 | NM_145290 | 5 | + | + | + |
| GPR135 | NM_022571 | 10 | + | + | + |
| GPR141 | NM_18179.1 | 1 | + | M+ | + |
| GPR146 | NM_138445.2 | 10 | + | M+ | + |
| GPR160 | NM_014373.2 | 6 | + | + | + |
| GPR19 | NM_006143.2 | 7 | + | + | + |
| GPR31 | NM_005299.2 | 8 | + | + | + |
| GPR32 | NM_001506.1 | 9 | + | + | + |
| GPR42/FFAR3 (GPR41) | NG_008348.2/NM_005304.3 | 12 | + | + | + |
| GPR63 | NM_030784.2 | 9 | + | + | + |
| GPR65 | NM_003608 | 2 | + | + | + |
| LGR4 | NM_018490 | 2 | + | + | + |
| LPHN1 | NM_001008701;NM_014921 | 5 | + | + | + |
| MAS1 | NM_002377 | 10 | + | + | + |
| MRGPRD | NM_198923 | 12 | + | + | + |
| MRGPRX1 | NM_147199 | 12 | + | + | + |
| MRGPRX4 | NM_054032 | 13 | + | + | + |
| OPN3 | NM_014322 | 10 | + | + | + |
| TAAR6 | NM_175067 | 12 | + | + | + |
| TAAR8 | NM_53278 | 13 | + | + | + |

UNLIKELY CANDIDATE, EITHER DEORPHANIZED OR BEARS HOMOLOGY TO GPCRS THAT DO NOT BIND PEPTIDES
GOOD CANDIDATE   GOOD CONTROL

FIG.5A

| Notes | Expression Profile |
|---|---|
| EMR family of protein receptors. Involved in adhesion, binds chondroitin sulfate and complement regulatory protein CD55 | |
| chemokine like receptor, binds to chemerin (Endorinology, 2012, 153(2):672-82) | |
| Duffy anitgen receptor for chemokines...a possibility | |
| will serve as good control | |
| Sperm cells, possible adhesion GPCR. Unlikely candidate | |
| nothing known | Brown Adipose Tissue, Brain, Pituitary |
| Only one article...shares no similarity with any other receptor | High in Bone Marrow, some in Spleen and Lung |
| nothing known | High in Heart, White Adipose Tissue, Liver, Muscle, Bone Marrow |
| nothing known | |
| high expression in the brain | Highest expression in Testes |
| deorphanized | Brain, Islets, Testes |
| Only 6 aa differences between 42 and 41 | Pancreatic Islets |
| possibly receptor for sphingosines | Highest in Brain |
| Note: Proton sensing??? Not a likely candidate  Note: LGR4 and 5 were deorphinized, and do not bind G proteins | |
| Note: Deorphinized | |
| beta alanine receptor, mas related | |
| itch receptor | |
| opsin related | |
| trace amine associated receptor | |
| probably chemosensory | |

SYSTEMS AND METHODS FOR DETERMINING A C-PEPTIDE RECEPTOR, C-PEPTIDE RECEPTOR, AND METHODS OF USING SAME

CROSS REFERENCE TO RELATED APPLICATION(S)

This application claims the benefit of U.S. Provisional Patent Application Ser. No. 61/696,646, filed Sep. 4, 2012, the entire disclosure of which is herein incorporated by reference.

BACKGROUND OF THE INVENTION

1. Field of the Invention

This disclosure is related to the field of locating specific ligand receptors, as well as to the use of such strategy to determine a C-peptide receptor.

2. Description of Related Art

The human body in its functions requires a very delicate balance of chemicals in order to process, transfer, and metabolize. The levels of key metabolites in a human body are only properly maintained within a known physiological range by normal action of body organs. Any repetitive change in the concentration of these known chemicals from these expected ranges is generally a sign of illness.

It has been recognized in a number of areas of medicine that identification of peptide receptors for peptides associated with various illnesses can be useful. It is commonly accepted that tissues becoming resistant to the actions of certain peptides can result in some of the chemical imbalances such as diabetes. Further, certain forms of cancerous tumors show increased numbers of certain peptide receptors. Therefore, the knowledge of peptide receptors can be used to selective target therapies.

Diabetes is a disease characterized by an elevated blood glucose concentration as a result of insufficient (or no) insulin production in the pancreas or, in some cases, by insulin resistance. In effect, the body's blood chemistry is regularly outside normal ranges because the blood glucose concentration is higher than it normally would be. This excess concentration can result in a variety of harms to the human body such as damage to tissues due to the excess glucose concentration. Specifically, excess glucose is commonly known to be harmful to blood vessel walls and can cause problems in blood circulation where such vessels are present. This can include damage to the kidneys, extremities, eyes, nerves, heart, and brain.

Diabetes is generally classified in two categories. Type I diabetes generally results when the pancreas creates little, and often no, insulin. In effect, pancreatic function is dramatically reduced or non-existent to the extent that the body simply cannot function with the amount of insulin available regardless of other factors. Type I diabetes is not totally understood, but does seem to have genetic components and may be connected to infections from certain viruses at certain life stages. It generally begins early in life. There are no known cures for Type I diabetes, and currently the only treatment options are monitoring of blood glucose levels and the use of external insulin sources to maintain blood glucose in a desired range.

Type II diabetes is characterized by either insulin resistance, or by the pancreas not producing sufficient insulin. The direct cause of Type II diabetes, is also currently unknown but it appears that a lack of exercise and excess weight can precipitate the onset of Type II diabetes. Most people with Type II diabetes have lived a good portion of their life without it and had workable pancreatic and insulin function prior to the diagnosis. While Type II diabetes is also generally incurable, it can be controlled through insulin therapy in the same way as Type I diabetes and onset can often be halted and/or reversed through lifestyle changes if detection occurs sufficiently early. Essentially, so long as sufficient insulin production capacity remains and insulin resistance is not too high, a controlled diet can allow the body to function correctly with the naturally occurring insulin that is available with Type II diabetes.

According to the International Diabetes Federation, there are currently 246 million diabetics worldwide and the number is expected to reach 380 million by 2025. In many cases, even chronic diabetes is a very controllable disease so long as the body's functions are correctly monitored and glucose (or insulin) is supplied to the body when appropriate. In effect, processes that are normally regulated automatically by the human body become the subject of external regulation and exogenous insulin administration. The prevalence of Type I diabetes is relatively small and generally comprises only about 5% of those with diabetes. Thus, Type II is the primary source of diabetes concerns and costs.

The number of individuals with Type II diabetes has risen dramatically in recent years. It is believed that a diet of processed food which has, in many cases, replaced a diet of unprocessed food for many households has, at least in part, led to this marked increase in the rise of diabetes. Further, the increase in average human weight, and an increased incidence of obesity, along with a general lack of exercise, are also likely contributing factors. Further, as diabetes is a very survivable disease if monitored and controlled, survivability for diabetics is also increasing resulting in additional numbers.

While both forms of diabetes are controllable, therapeutic treatment has focused on the application of external insulin and glucose. Thus, an individual with diabetes is generally doomed to a future of monitoring and external supply. Thus, while an individual can live out their life quite productively with diabetes, the disease causes significant economic costs, lifestyle changes, and a risk of complications from inaccurate monitoring or control that never goes away. Particularly in the long term, diabetes can lead to complications for the individual, including microvascular complications that can result in decreases to quality of life, and even premature death.

It is understood that a lack of insulin, or even an overabundance of insulin, can create medical problems. Even with good control over insulin levels, there is a much increased risk that medical complications can arise when one is on insulin therapy simply because external control of insulin levels will likely never be as accurate as the body's internal controls (when they work correctly). For example, peripheral vascular disease is common among diabetics and generally will occur in Type I diabetics, to some degree, in virtually all cases over a long enough time period. In a large number of cases, this complication, which decreases blood flow to the extremities, can result in amputation of one or more extremities. Indeed, diabetes is the leading cause of non-traumatic leg amputations in the United States.

The production of insulin by the pancreas actually produces two molecules. These molecules are insulin and C-peptide. C-peptide is a protein chain derived from the insulin precursor. For every molecule of insulin created, a molecule of C-peptide is created. C-peptide is metabolized by an individual's kidney at a much slower rate than insulin is metabolized by the liver, so C-peptide can make a useful marker for determining a body's insulin production, regardless of what may be occurring that results in insulin being supplied to the body.

For many years C-peptide was thought to be biologically inert and to have little relevance in medical science beyond its use as a marker for insulin production. However, recent studies have indicated that C-peptide binds to a variety of tissues, initiates intracellular signaling cascades distinct from insulin, and exerts biological activities that may complement insulin action. Interestingly, C-peptide appears to counteract many of the deleterious effects of excess insulin in several tissues, including kidney and vasculature. This suggests that C-peptide may represent a novel therapeutic for the treatment of some diabetes-associated diseases (complications), such as peripheral vascular disease and diabetic nephropathy.

The presence and use of C-peptide may protect against blood vessel damage and deleterious alterations in blood flow that can occur even with well-controlled diabetes due to occurrences of excess (or insufficient) insulin. Alternatively, microvascular complications, including peripheral vascular disease, diabetic retinopathy, diabetic neuropathy, and diabetic nephropathy, may actually be directly related to the lack of C-peptide, not directly to insulin or blood glucose levels.

Currently treatment for many diabetic-related complications are simply to better control blood glucose levels (that is to avoid the insulin imbalances that are believed to cause them) and eliminate known risk factors, such as smoking. While this can be effective, until external insulin monitoring and supply can become as effective as the body's natural internal processes, maintaining the body in perfect balance with any insulin therapy is not possible. Currently, there is no real pharmaceutical treatment directly acting on the complications resulting from diabetes as pharmaceutical treatments focus on either controlling the insulin levels, or trying to better sensitize the body to insulin.

Treatment with C-peptide agonists may be an important adjuvant therapy in Type I diabetes since even in well controlled Type I diabetes vascular complications are highly likely to eventually occur and that may be because of a lack of C-peptide and not failure to control insulin levels. As type I diabetics lack beta cell function, and therefore are C-peptide deficient as well as being insulin deficient, some diabetic complications may result from insufficient C-peptide and not just inaccurate control of insulin. Current methods of insulin therapy, while replacing the specific need for insulin by the body, do not provide C-peptide and therefore a loss of C-peptide may create, or exacerbate, certain complications resulting from Type I diabetes.

Likewise Type II diabetics, in which there is a high incidence of vascular disease, appear to develop some C-peptide resistance, so treatment with C-peptide sensitizers in addition to insulin sensitizers, could potentially help alleviate diabetic complications for Type H diabetics. Thus, the ability to supply the body of a diabetic with C-peptide therapy, while it may not correct or reduce the underlying insulin production function, may help to reduce complications from either form of diabetes.

While the above indicates that C-peptide replacement treatments can be valuable, in order to produce C-peptide agonists and sensitizers, it is necessary to identify the C-peptide receptor, which has thus far eluded detection. There has been speculation that alpha-enolase is a potential C-peptide receptor. However, this has not been confirmed and those skilled in the art are doubtful as typically enolases are intracellular enzymes and not receptors.

SUMMARY OF THE INVENTION

Because of these and other problems in the art, described herein, among other things, is a methodology for matching peptides to cognate receptors. In effect, it is a new methodology for locating specific receptors for peptides of interest. Once such a receptor is located, it can then be used as a target for therapies related to that peptide.

In an embodiment, there is described herein a system, method, means, and non-transitory computer readable medium incorporating instructions for locating a G protein coupled receptor (GPCR) for a selected peptide, the method comprising: screening biological matter expected to be responsive to said selected peptide for GPCR expression; create list of expressed GPCRs; remove GPCRs that have a known other function from said list; organize said expressed GPCRs on list into a hierarchical order; test a highest ordered GPCR on said list that has not yet been tested for responsiveness; and repeat said test until a responsive GPCR is found or no more GPCRs not yet tested remain on said list.

In an embodiment of the method, said selected peptide comprises C-peptide.

In an embodiment of the method, said test said highest ordered GPCR on said list that has not been tested comprises transfecting said GPCR with siRNA and evaluating if there is a negative response to said specified peptide.

In an embodiment of the method, said expressed GPCRs includes GPR146.

DESCRIPTION OF THE PREFERRED EMBODIMENT(S)

Described herein are systems and methods for the determination of a peptide receptor. The present systems and methods are useable to determine a receptor for any peptide provided that the receptor is a G protein coupled receptor (GPCR). As GPCRs are utilized in a large percentage of medications, and are sensitive to a large number of ligands, even being limited to detection of GPCR receptors still provides a potentially highly valuable test methodology and system. Further, there are a very large number of potential GPCRs and conventional testing can determine only if a selected GPCR is, or is not, a receptor of a selected. There has previously been no methodology for improved hierarchical ranking to select more likely candidate GPCRs on which to perform such testing.

Figure 1A:
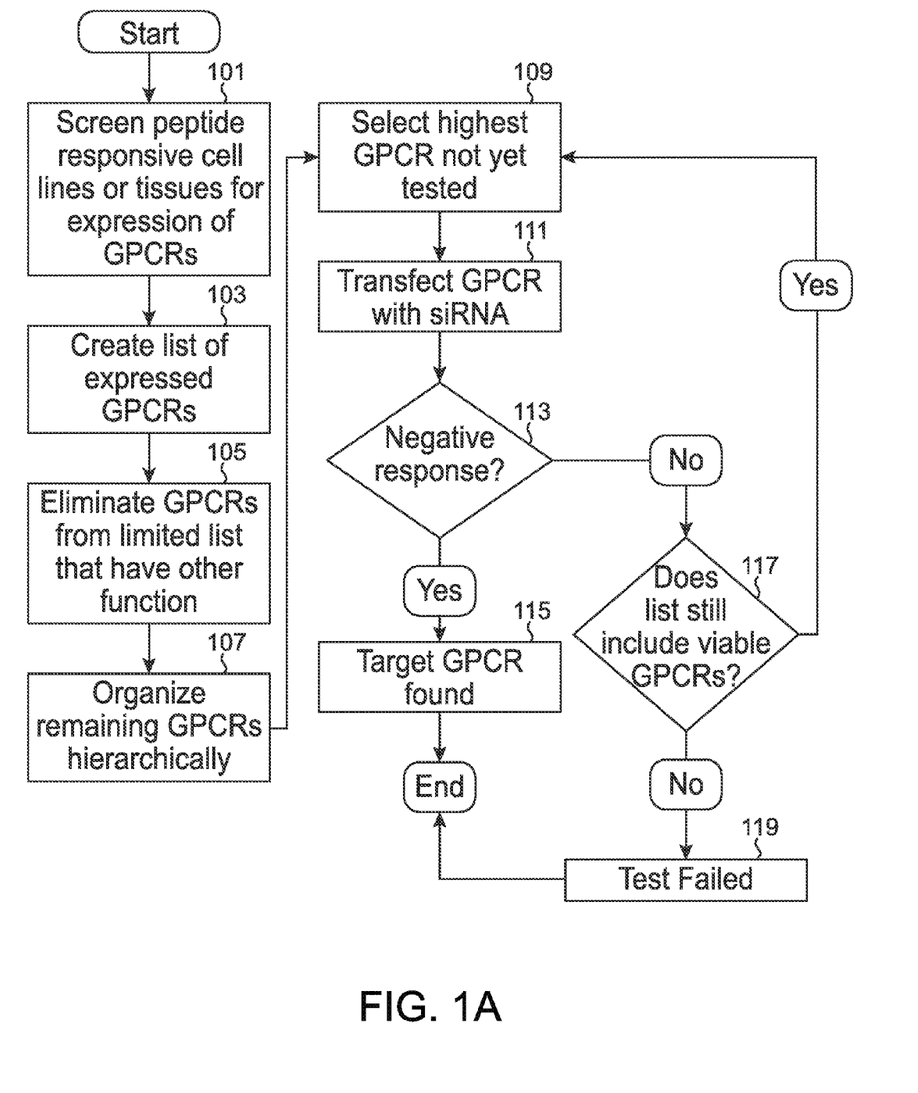
FIG. 1A provides a flowchart of the steps of an embodiment of a deductive ligand-receptor matching strategy.
Figure 1B:
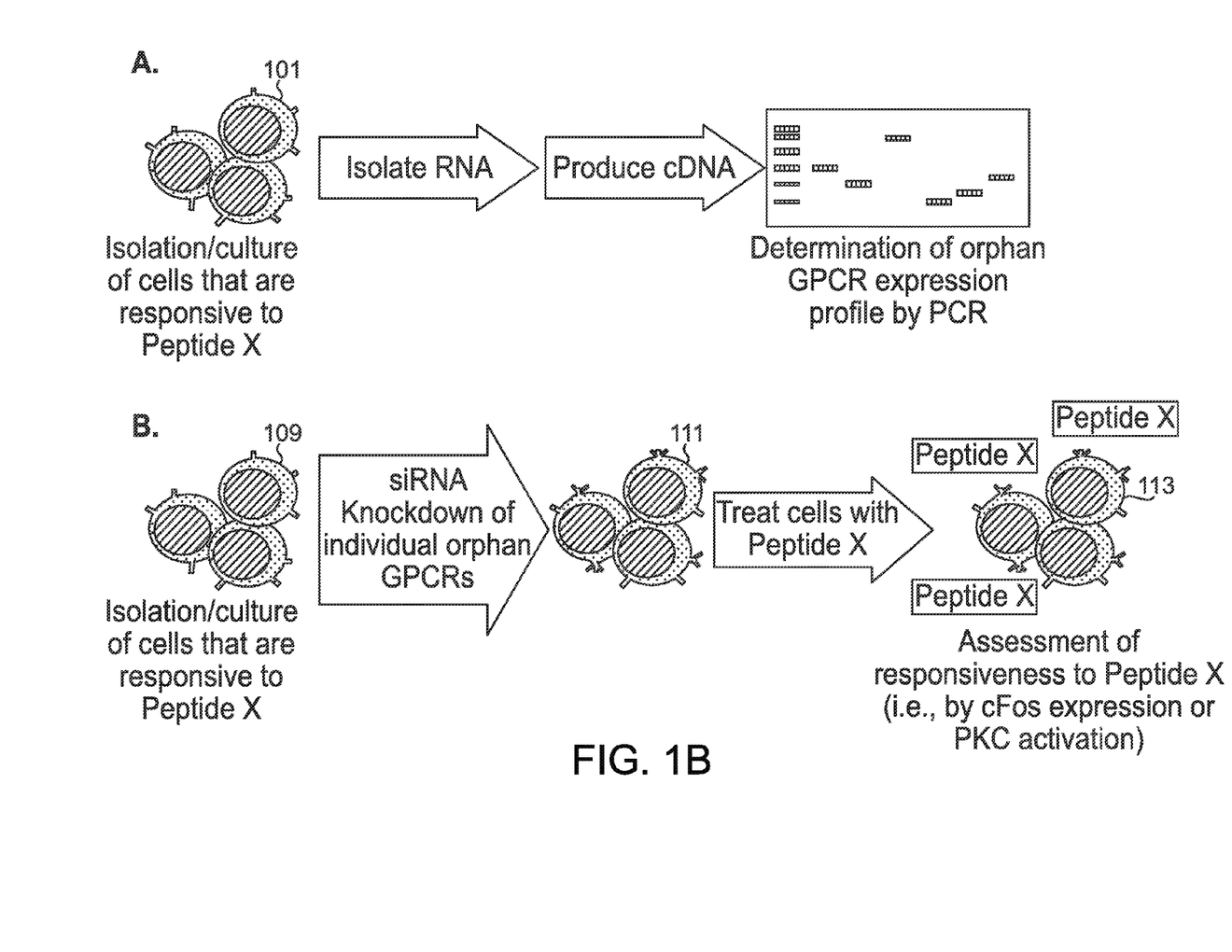
FIG. 1B provides a graphical representation of an embodiment of a deductive ligand-receptor matching strategy.

In order to determine a particular peptide receptor, the following general method is performed as shown in the charts of FIGS. 1A and 1B. First cell lines or tissues that are known to be responsive to the peptide of interest are screened for the expression of known GPCRs using multiplex PCR (101).

This will result (103) in a shortened list of potential receptor candidates since the target GPCR would need to be present in a responsive cell or tissue in order for that cell or tissue to be responsive. This list can then generally be further shortened (105) based on the elimination of GPCRs of already known other function, or which are unlikely to be appropriate receptors for other reasons known to one of ordinary skill in the art. This shortened list can then be organized hierarchically (107) based on the presence or absence of the particular GPCR in all cells/tissues, many cells/tissues, or limited cells/tissues that are responsive to the peptide of interest.

Once this list of potential GPCRs is determined, the highest ranked (109) untested responsive tissue or cell line is transfected with siRNA against the candidate receptors (111) to assess responsiveness of those cells to the peptide as a marker of activation. One would expect one of the highest ranked GPCRs to show a negative response (loss of sensitivity to the peptide) indicating a likely match. The process is repeated (113) for the GPCRs in the ranked hierarchical order until a likely match is found (115), or it is determined that the method has likely failed (119) as no items remain in the list or a sufficient number of tests have left only sufficiently unlikely remaining candidates (117) to justify costs of additional testing.

C-peptide binding is generally not displaced by insulin, IGFI, or IGFII. Further, C-peptide initiates intracellular signaling cascades that are usually associated with GPCR activation and cellular actions are pertussis toxin sensitive. Therefore, it is expected that the C-peptide receptor is a GPCR and particularly an orphan GPCR. Therefore, the methodology included herein would be expected to be useful to determine at least one C-peptide receptor. An implementation of the above methodology to locate a C-peptide receptor is discussed below.

Figure 2:
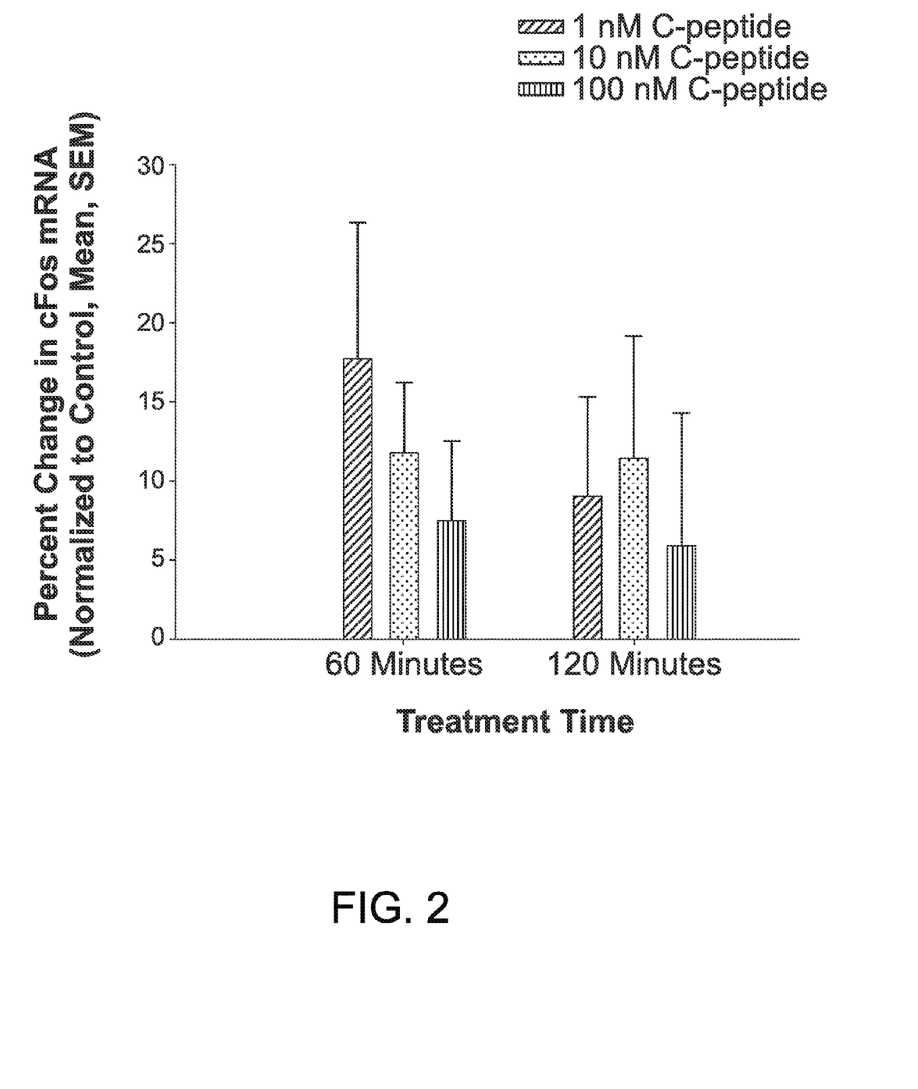
FIG. 2 shows a bar chart of how the treatment of C-peptide leads to an increase in cFos mRNA expression in KATOIII cells.
Figure 3:
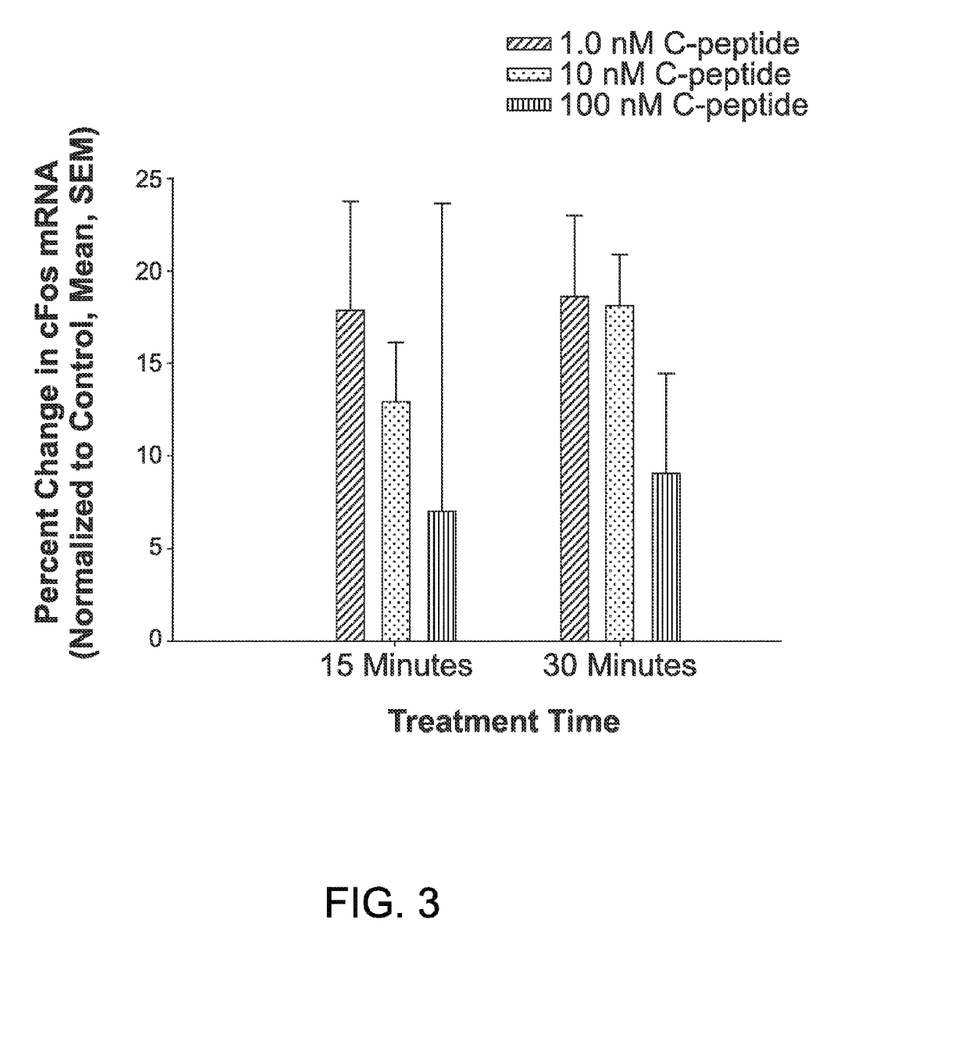
FIG. 3 shows a bar chart of how the treatment of C-peptide leads to an increase in cFos mRNA expression in HEK293 cells.
Figure 4:
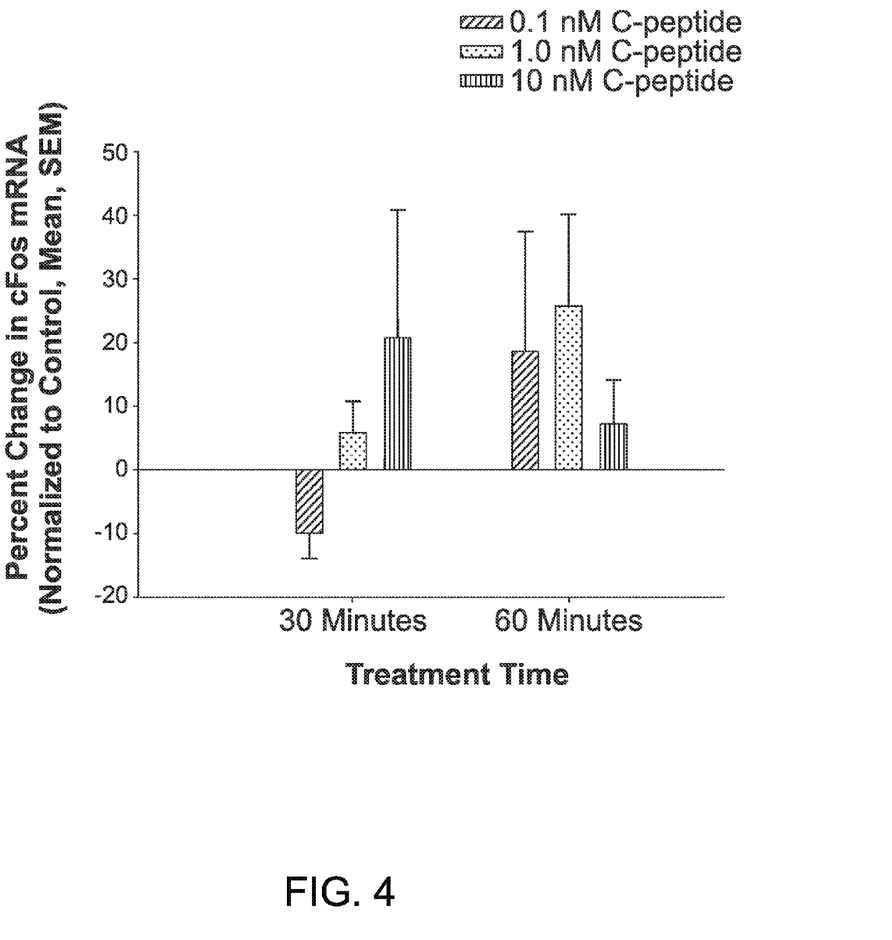
FIG. 4 shows a bar chart of how the treatment of C-peptide leads to an increase in cFos mRNA expression in TF-1 cells.
Figure 5A:
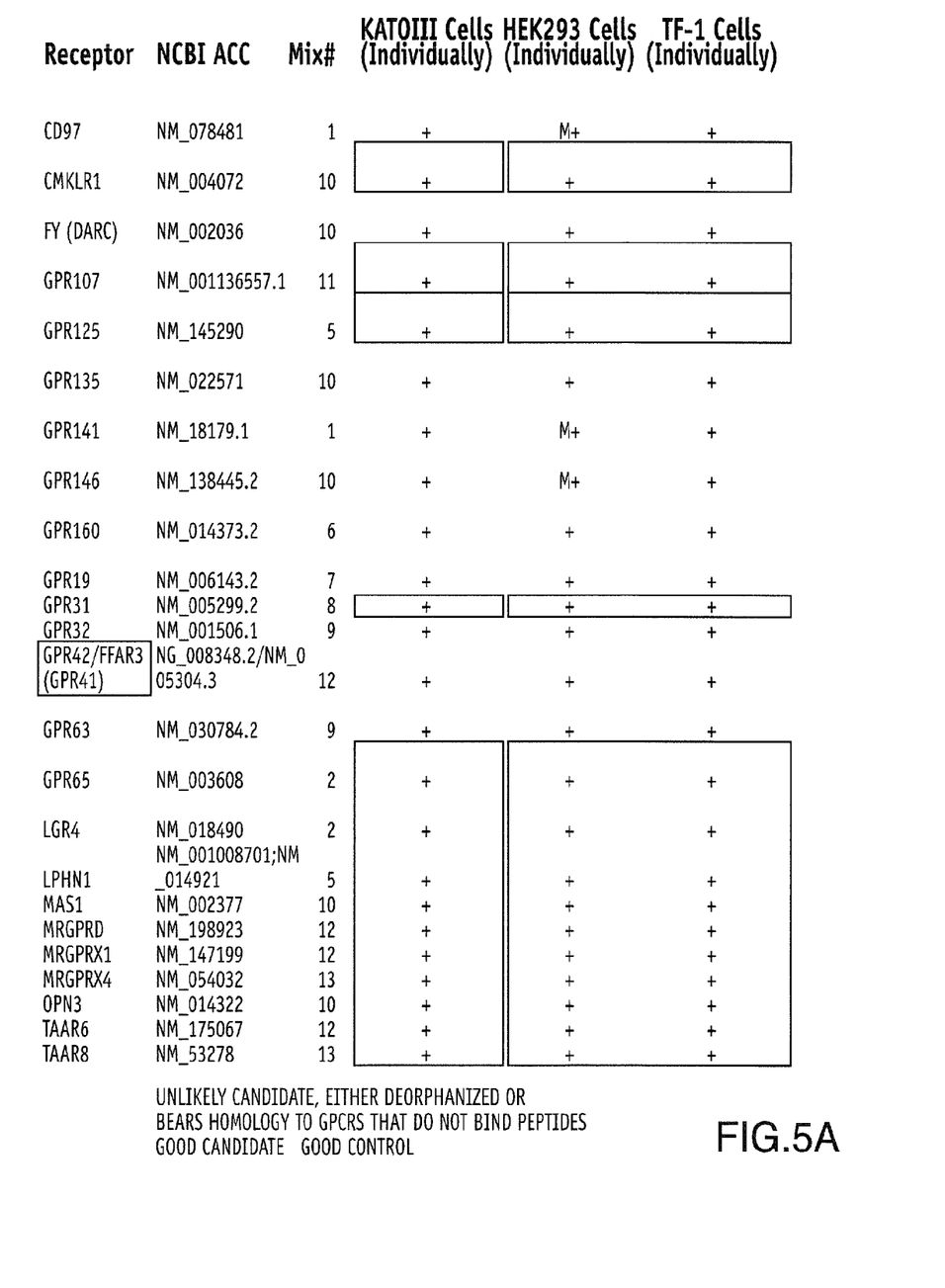
FIGS. 5A and 5B show a table of the expression of known orphan GPCRs from the cell lines of FIGS. 2-4 along with GPCRs eliminated as unlikely candidates.
Figure 5B:
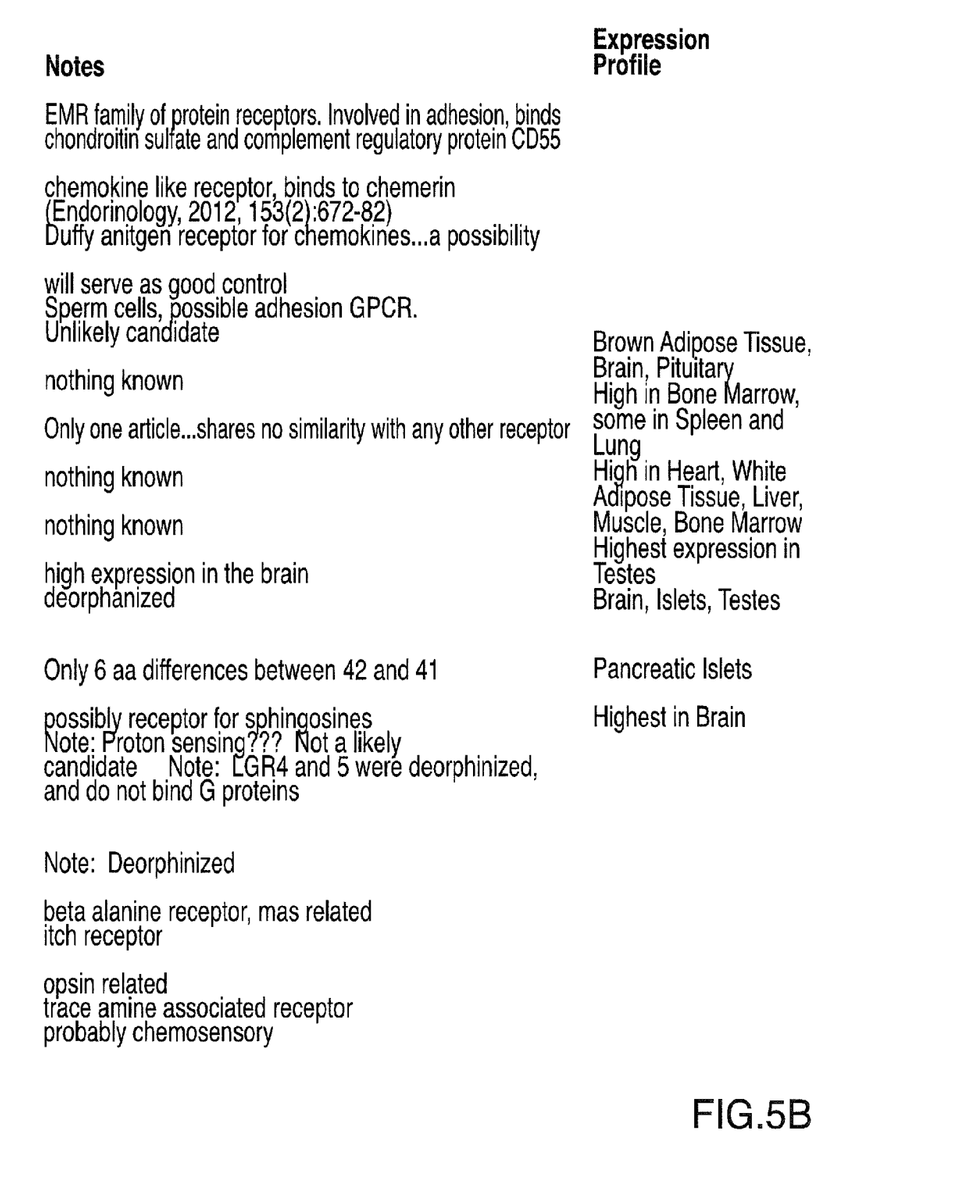

In utilizing the methodology to determine a C-peptide receptor, three human cell lines were determined (101) to respond to treatment with C-peptide with an up regulation of cFos message as determined by RT-PCR. These three were KATOIII (Human Stomach Carcinoma), HEK 293 (human embryonic kidney cells) and TF-1 (an erythroleukemia cell line). The results of tests to show responsiveness are provided graphically in FIGS. 2, 3, and 4. When these three cell lines were screened for the expression of known orphan GPCRs (103), 24 of the approximately 125 orphan GPCRs were expressed by all three cell types as indicated by the table of FIG. 5. Using bioinformatics, the pool of FIG. 5 can be narrowed (105) by eliminating any candidates already matched to other ligands or that had significant homology to GPCRs that bind to non-peptide targets (15 in this case). This is also shown in FIG. 5 with the items that are eliminated darkened. One GPCR (GPR107) could be eliminated as it was recently determined that this was the cognate receptor for neurostatin. This also allowed it to be used as a convenient control as evidenced later herein.

Amongst available candidates, evaluation of expression patterns of the receptors can be taken into consideration to rank those available options. Specifically, a receptor for C-peptide would be expected to be expressed in kidney, skeletal muscle, pancreatic, adipose tissue, and bone marrow, since all these tissues are known to respond to a C-peptide treatment. This provided a hierarchical ordered list (107) of preferred candidates:

1. GPR146
2. GPR19
3. GPR135
4. GPR141
5. GPR160
6. GPR42 and GPR41

GPR41 and GPR42 were ranked together due to structural similarity. GPR146 was the top candidate in the hierarchical list as it is known to be produced by all tissues responsive to C-peptide listed above. GPR19 was produced by many, but not all, and therefore was the indicated second candidate.

Figure 6:
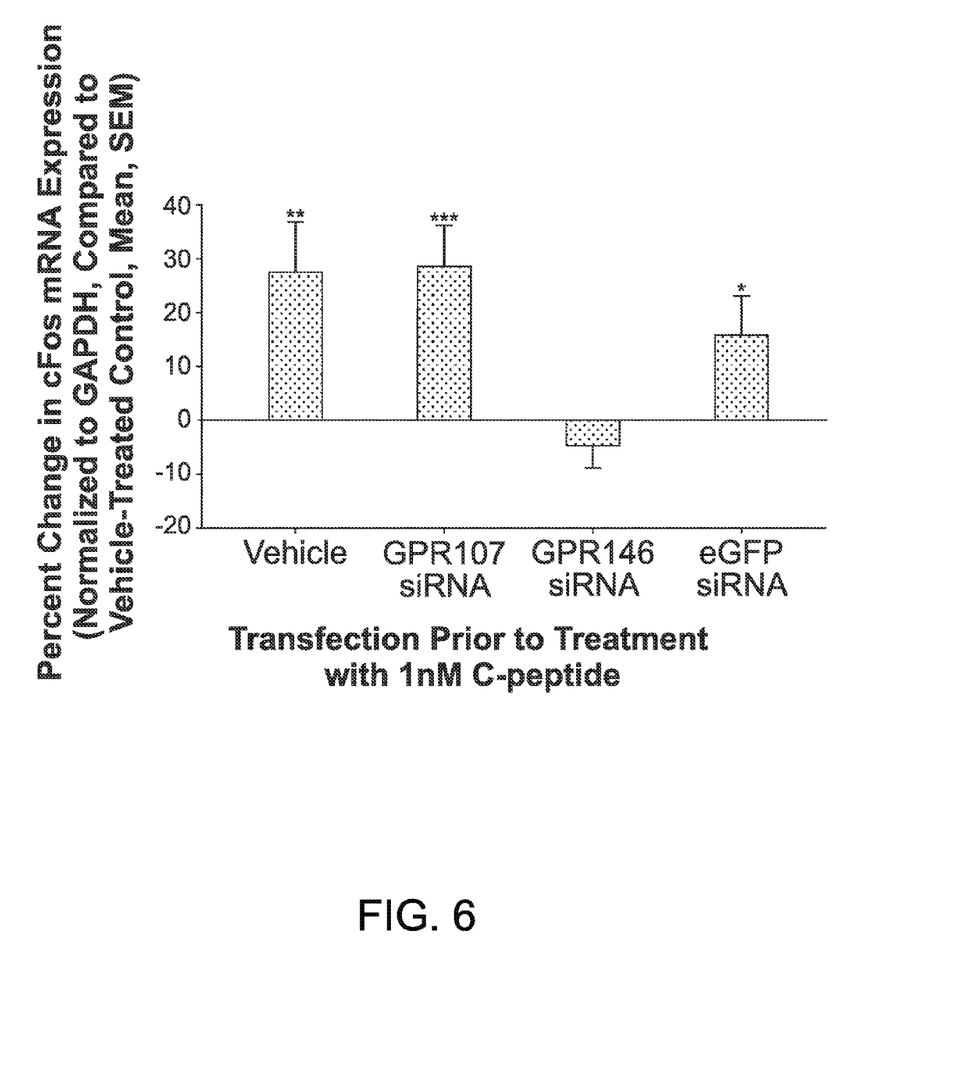
FIG. 6 shows the compromise of GPR146 ablates C-peptide-induced cFos expression in KATOIII cells.

Once the hierarchical candidates were identified and ranked, KATOIII cells were then transfected with siRNA (Integrated DNA technologies) (111) directed against either GPR107 (control), GPR146 (most likely candidate not yet tested) or eGFP (green fluorescent protein—control) using Lipofectamine 200 (Invitrogen). Five hours later, the media was changed to serum free control media (ATCC) and the serum was starved overnight. Twenty-four (24) hours after transfection with siRNA, cells were treated with 1 nmole C-peptide (Phoenix Pharmaceuticals) for 1 hour, then lysed and RNA were isolated using an RNeasy Kit (Qiagen). RNA was used as a template from the production of cDNA, and changes in cFos expression were determined using RT-PCR (BioRad 2x iQ SyberGreen Master Mix, using a BioRad CFX real time system). C-peptide led to an increase in cFos in KATOIII cells that were transfected with a Vehicle (Lipofectamine 2000 alone, no siRNA), GPR107 siRNA, or sGFPO siRNA. However, cells in which GPR146 was compromised failed to respond to C-peptide as shown in FIG. 6. As this produced the desired negative response (113), GPR146 was the target GPCR (115). The receptiveness of GPR146 to C-peptide has since been verified by additional conventional tests While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A method for locating a G protein coupled receptor (GPCR) for a selected peptide, the method comprising:
    screening a plurality of different biological matters expected to be responsive to said selected peptide for GPCR expression;
    create a list of GPCRs expressed by all said plurality of biological matters;
    remove GPCRs from said list that have a known other function;
    organize said expressed GPCRs on said list into a hierarchical order wherein when said GPCR is given a higher rank, it is produced in at least as many tissues responsive to said selected peptide as any of said GPCRs of a lower rank;
    test a highest ordered GPCR on said list that has not yet been tested for responsiveness;
    repeat said test until a responsive GPCR is found or no more GPCRs not yet tested remain on said list.

2. The method of claim 1 wherein said selected peptide comprises C-peptide.

3. The method of claim 1 wherein said test comprises transfecting one of said plurality of different biological matters with siRNA directed against said highest ordered GPCR and evaluating if there is a negative response to said specified peptide.

4. The method of claim 1 wherein said expressed GPCRs includes GPR146.

* * * * *